United States Patent
Kahlert et al.

(10) Patent No.: US 8,207,368 B2
(45) Date of Patent: Jun. 26, 2012

(54) STABILIZATION OF DIESTERS OF DICARBONIC ACID

(75) Inventors: Steffen Kahlert, Leichlingen (DE); Johannes Kaulen, Odenthal (DE); Erasmus Vogl, Leverkusen (DE)

(73) Assignee: LANXESS Deutschland GmbH, Leverkusen (DE)

( * ) Notice: Subject to any disclaimer, the term of this patent is extended or adjusted under 35 U.S.C. 154(b) by 410 days.

(21) Appl. No.: 12/293,693

(22) PCT Filed: Apr. 11, 2007

(86) PCT No.: PCT/EP2007/003200
§ 371 (c)(1),
(2), (4) Date: Nov. 11, 2009

(87) PCT Pub. No.: WO2007/121857
PCT Pub. Date: Nov. 1, 2007

(65) Prior Publication Data
US 2010/0069658 A1    Mar. 18, 2010

(30) Foreign Application Priority Data

Apr. 22, 2006 (DE) .................. 10 2006 018 843

(51) Int. Cl.
*C07C 68/08* (2006.01)

(52) U.S. Cl. ........................................ 558/260; 558/261
(58) Field of Classification Search ................. None
See application file for complete search history.

(56) References Cited

U.S. PATENT DOCUMENTS

| 4,565,648 A | 1/1986 | Kopp et al. |
| 5,738,888 A | 4/1998 | Cirigliano et al. |
| 6,488,859 B2 | 12/2002 | Alexandratos et al. |

FOREIGN PATENT DOCUMENTS

| EP | 0355007 B1 | 2/1990 |
| JP | S43-27095 | 11/1968 |
| WO | 2005123682 A1 | 12/2005 |

OTHER PUBLICATIONS

International Search Report from co-pending Application PCT/EP2007/003200 dated Apr. 11, 2007, 19 pages.
XP-002445031 & JP 46 037810B, Sumitomo Chem. Co, Ltd. Nov. 8, 1971.
XP-002445176 & JP 48 004016B, Hodogaya Chem. Co. Ltd. Feb. 5, 1973.

*Primary Examiner* — Yong Chu
*Assistant Examiner* — Michael Barker
(74) *Attorney, Agent, or Firm* — Nicanor A. Kohncke

(57) ABSTRACT

By using phosphorus compounds, diesters of dicarbonic acid may be stabilized against thermal and chemical decomposition over a relatively long period. Mixtures of diesters of dicarbonic acid and phosphorus compounds are outstandingly suitable for preserving foods.

6 Claims, No Drawings

STABILIZATION OF DIESTERS OF DICARBONIC ACID

CROSS REFERENCE TO RELATED PATENT APPLICATIONS

The present patent application claims the right of priority under 35 U.S.C. §119 (a)-(d) and 35 U.S.C. §365 of International Application No. PCT/EP2007/003200, filed 11 Apr. 2007, which was published in German as International Patent Publication No. WO 2007/121857 A1 on 1 Nov. 2007, which is entitled to the right of priority of German Patent Application No. DE 10 2006 018 843.8 filed on 22 Apr. 2006.

The present invention relates to the use of phosphorus compounds as stabilizers of diesters of dicarbonic acid, mixtures containing diesters of dicarbonic acid and phosphorus compounds, and also the use of these mixtures for preserving foods and materials.

Diesters of dicarbonic acid are used, inter alia, for preserving foods, in particular drinks, as components of antimicrobial reagents, for deactivating enzymes in fermentation processes, or for the synthesis of fine chemicals or polymers. Diesters of dicarbonic acid are used, in addition, for example as catalysts for the oxidation of amines, or for synthesis, for example in the introduction of protecting groups.

It is known that the stability of diesters of dicarbonic acid can be relatively low at room temperature, and in particular at elevated temperature. In particular during purification, for example in purification by distillation, or during relatively long storage, decomposition of diesters of dicarbonic acid can therefore occur. This decomposition can impair the quality and purity of the diesters of dicarbonic acid. In addition, the decomposition generally proceeds the more rapidly the more impurities are present. High purity and stabilization of diesters of dicarbonic acid are therefore highly desirable.

Methods for improving the thermal stability of diesters of dicarbonic acid are already known from the prior art. For instance, it is proposed, for example, to stabilize dialkyl pyrocarbonates by adding metal sulphates (cf. JP-A 48-4016). A disadvantage of this method, however, is that these metal sulphates are sparingly to poorly miscible with the diesters of dicarbonic acid.

In addition, it is known to stabilize diesters of dicarbonic acid by adding boron compounds (cf. JP-A 46-37810). However, a disadvantage in this case is the toxicity of the corresponding boron compounds. Usage in foods does not come into consideration for these additions.

In addition, carbonyl compounds and also heteroanalogous carbonyl compounds have been proposed as additives increasing the storage stability of solutions of diesters of dicarbonic acid in solvents inert to diesters of dicarbonic acid (cf. DE-A 3231397). However, solutions of diesters of dicarbonic acid in customary aprotic solvents scarcely come into consideration as an addition to foods. In addition, stabilizing effects may only be achieved using relatively high percentage amounts of additions.

There was therefore a requirement for stabilizers which are suitable for protecting diesters of dicarbonic acid effectively against thermal breakdown.

Surprisingly, it has now been found that diesters of dicarbonic acid can be stabilized by addition of phosphorus compounds against thermal and/or chemical breakdown reactions such as can occur, for example in storage or purification such as purification by distillation.

The present invention therefore relates to the use of at least one phosphorus compound for stabilization of diesters of dicarbonic acid against chemical and/or thermal breakdown reactions.

The diesters of dicarbonic acid are preferably compounds of the general formula (I)

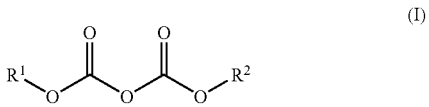

where
$R^1$ and $R^2$ independently of one another are straight-chain or branched $C_1$-$C_8$-alkyl, cycloalkyl, $C_2$-$C_8$-alkenyl, $C_2$-$C_8$-alkynyl or benzyl,
each of which is optionally monosubstituted to polysubstituted, identically or differently by halogen; nitro; cyano; $C_1$-$C_6$-alkoxy; dialkylamino; or are phenyl which is optionally monosubstituted to polysubstituted, identically or differently by halogen; nitro; cyano; alkyl; haloalkyl; alkoxy; haloalkoxy; acyl; acyloxy; alkoxycarbonyl; carboxyl,
preferably
$R^1$ and $R^2$ independently of one another are straight-chain or branched $C_1$-$C_8$-alkyl, $C_2$-$C_8$-alkenyl or benzyl,
particularly preferably
$R^1$ and $R^2$ independently of one another are straight-chain or branched $C_1$-$C_5$-alkyl, $C_3$-alkenyl or benzyl,
and very particularly preferably
$R^1$ and $R^2$ independently of one another are methyl, ethyl, isopropyl, tert-butyl, tert-amyl, allyl or benzyl.

The stabilizers are phosphorus compounds, preferably compounds of phosphorus with oxygen, more preferably containing at least one phosphorus-oxygen bond, particularly preferably compounds from the series of phosphorus oxides and phosphorus-oxygen acids and derivatives thereof.

Those which may be mentioned as phosphorus-oxygen acids by way of example are: ortho and meta acids of the general formulae $H_3PO_n$ and $HPO_{n-1}$ where n=2, 3, 4 and 5, diacids of the general formula $H_4P_2O_n$ where n=4, 5, 6, 7 and 8, and also polyphosphoric acids of the general formula $H_{n+2}P_nO_{3n+1}$ where n=3-15 000.

As derivatives of the phosphorus-oxygen acids, those which may be mentioned are, in particular, salts and esters thereof. As examples of esters, those which may be mentioned are mono-, di- and trialkyl esters, mono-, di- and trialkenyl esters, mono-, di- and triaryl esters and also esters with sugar derivatives or glycerol derivatives. The alkyl radicals in the said mono-, di- and trialkyl esters are, for example, methyl, ethyl, n-propyl, isopropyl, n-butyl, sec-butyl, tert-butyl radicals. The esters can also be present as salts, for example alkali metal or alkaline earth metal salts, such as sodium, potassium, magnesium or calcium salts.

As further derivatives of the phosphorus-oxygen acids, mention may be made of compounds which in addition contain at least one phosphorus-carbon bond. Examples of phosphorus-carbon-containing compounds of this type are derivatives of phosphonic acids, phosphonous acids or phosphinic acids and esters thereof. Examples of esters which may be mentioned are mono-, di- and trialkyl esters, mono-, di- and trialkenyl esters, mono-, di- and triaryl esters and also esters with sugar derivatives or glycerol derivatives. The alkyl radicals in the said mono-, di- and trialkyl esters are, for example, methyl, ethyl, n-propyl, isopropyl, n-butyl, sec-butyl, tert-butyl radicals. The esters can likewise be present as salts, for example alkali metal or alkaline earth metal salts such as sodium, potassium, magnesium or calcium salts.

As phosphorus compounds, very particular preference is given to phosphorus pentoxide ($P_2O_5$), hypophosphorous acid ($H_3PO_2$), phosphorous acid ($H_3PO_3$), aqueous or crystalline phosphoric acid ($H_3PO_4$), pyrophosphoric acid, metaphosphoric acid, polyphosphoric acids, dimethyl phosphate, trimethyl phosphate, phosphates such as sodium hydrogen phosphates or ammonium hydrogen phosphates, oleylphosphate, phytic acid, phosphorylcholine, adenosine 3'-monophosphoric acid, 2-phosphonobutane-1,2,4-tricarboxylic acid, aminotrismethylenephosphonic acid, diethylenetriaminepentamethylenephosphonic acid or phosphonic-acid-group-containing ion exchangers, such as, for example disclosed by WO 2000001458 or by EP-A 355007.

The phosphorus compounds can be used as pure substances or as aqueous or alcoholic solutions. The compounds can equally be dissolved in advance in pyrocarbonates or other suitable solvents. The phosphorus compounds can also be immobilized on surfaces, for example glass surfaces.

In addition, of course, use can be made of the different reactive phosphorus-halogen compounds which even in the presence of only small amounts of water hydrolyse, in situ, to give the abovementioned phosphorus compounds. Examples of these are phosphorus trichloride or phosphoryl chloride.

The said stabilizers are generally used in an amount of 0.01 to 100 000 ppm, preferably in an amount of 0.1 to 10 000 ppm, particularly preferably in an amount of 0.1 to 3000 ppm, very particularly preferably in an amount of 0.1 to 2000 ppm, based on the diesters of dicarbonic acid or mixture thereof.

As a result of the use according to the invention, it is possible to stabilize diesters of dicarbonic acid in general against thermal and chemical breakdown reactions. Such breakdown reactions occur, for example, in storage.

The diesters of dicarbonic acid stabilized according to the invention are distinguished by improved storage stability. For instance, the diesters of dicarbonic acid stabilized in this manner can be stored for a plurality of months at room temperature without decomposition of the diesters of dicarbonic acid being observed.

The present invention further relates to mixtures containing one or more diesters of dicarbonic acid of the formula (I) illustrated above and one or more of the above generally and preferably described phosphorus compounds generally in an amount of 0.01 to 100 000 ppm, preferably in an amount of 0.1 to 10 000 ppm, particularly preferably in an amount of 0.1 to 3000 ppm, very particularly preferably in an amount of 0.1 to 2000 ppm, based on the diesters of dicarbonic acid or mixture thereof. Very particular preference is given to mixtures of at least one diester of dicarbonic acid of the formula (I), in particular dimethyl dicarbonate and/or diethyl dicarbonate with one or more phosphorus compounds from the series $P_2O_5$, $H_3PO_2$, $H_3PO_3$, aqueous or crystalline $H_3PO_4$, pyrophosphoric acid, metaphosphoric acid, polyphosphoric acids, dimethyl phosphate, trimethyl phosphate, phosphates such as sodium hydrogen phosphates or ammonium hydrogen phosphates, oleyl phosphate, phytic acid, phosphorylcholine, adenosine 3'-monophosphoric acid, 2-phosphonobutane-1,2,4-tricarboxylic acid, aminotrismethylenephosphonic acid, diethylenetriaminepentamethylenephosphonic acid, phosphorus trichloride, phosphoryl chloride or phosphonic-acid-group-containing ion exchangers.

The inventive mixtures can be stored over a period of a plurality of months without decomposition of the diesters of dicarbonic acid present therein occurring.

The inventive mixtures are outstandingly suitable for preserving foods and in particular drinks against infection and/or decomposition by microorganisms, such as, for example, bacteria, fungi or yeasts.

The present invention likewise relates to the use of the inventive mixtures for preservation of foods and drinks.

The diesters of dicarbonic acid stabilized according to the invention are outstandingly suitable, for example, as cold disinfectants for still or carbonated drinks such as soft drinks, vitamin drinks, fruit juice drinks, tea drinks, alcoholic or dealcoholized wine drinks, fruit punches or some beers. Customarily, for this the diesters of dicarbonic acid are added in amounts between 10 and 250 ppm close in time to packaging the drinks. Admixture to the drinks is performed using special metering pumps. The diesters of dicarbonic acid act so as to control a series of microorganisms such as fermentative yeasts, moulds or fermentative bacteria. Examples which may be mentioned here are for instance *Saccharomyces cerevisiae, Mycoderma, Brettanomyces* spp, *Lactobacillus brevis, Lactobacillus buchneri* and many others.

Thermal breakdown reactions of diesters of dicarbonic acid also occur, furthermore, in particular in the workup or distillation of diesters of dicarbonic acid as carried out, for example, in the context of the production method for diesters of dicarbonic acid. By means of the inventive use of phosphorus compounds it is possible to distil diesters of dicarbonic acid with relatively low losses and in relatively high purity.

The present invention therefore further relates to a method for the purification by distillation of diesters of dicarbonic acid, by admixing one or more diesters of dicarbonic acid of the above-specified formula (I) with one or more of the above generally and preferably described phosphorus compounds, generally in an amount of 0.01 to 100 000 ppm, preferably in an amount of 0.1 to 10 000 ppm, in each case based on the diesters of dicarbonic acid or mixture thereof, and subsequently distilling the mixture at a pressure of 5 to 100 mbar, preferably 10-70 mbar, and a temperature between 30 and 120° C., preferably between 40 and 90° C. Distillation columns customary in industry come into consideration for the distillation.

The yields of diesters of dicarbonic acid in the distillation are customarily >99%.

The present invention is described with reference to specific details of particular embodiments thereof. It is not intended that such details be regarded as limitations upon the scope of the invention except insofar as and to the extent that they are included in the accompanying claims. The examples hereinafter are intended to illustrate the subject matter of the invention without, however, restricting it thereto. As used in this specification and the appended claims, the singular forms "a," "an," and "the" include plural referents unless the content clearly dictates otherwise.

EXAMPLE 1

Corresponding to the data in Tables 1-6, in each case defined amounts of a defined high-purity diester of dicarbonic acid and the respectively stated additions were weighed in a 10 ml round-bottomed flask equipped with a magnetic stirrer. The exact amounts of the additions used in each case are likewise given in the tables.

The round-bottomed flask was tightly closed by a septum. In this septum was situated an orifice in which a Teflon tube was attached, which was passed into a vertical silicone-oil-filled 50 ml burette calibrated to 0.1 ml. On the scale of the burette, the amount of the carbon dioxide developing as a result of the decomposition of the diester of dicarbonic acid could be read off. The flask was promptly lowered into a constant temperature oil bath (stirred at 500 rpm) as specified in Tables 1-6 for the respective experiment. The depth of immersion of the flask was 2.0 cm.

After the respectively stated time, generally after 1, 2, 5, 10 and 15 minutes, the gas volume was read off. The gas volume is an index of the degree of decomposition of the diesters of dicarbonic acid to give $CO_2$. It thus inversely reflects the degree of stabilization by the additions tested.

In most cases the experiments were repeated in order to ensure reproducibility. Meaningful reproducibility was present in each case.

The results may be taken from the tables. High-purity pyrocarbonate, in the observed time, released little carbon dioxide, but even contact with small amounts of silica gel, manganese dioxide or else only rough surfaces such as scratched glass drastically accelerated decomposition. Small amounts of the stabilizers were sufficient for effective reduction of the decomposition.

The fewer gaseous decomposition products diesters of dicarbonic acid release under temperature stress, the more favourably does distillation under vacuum proceed.

TABLE 1

| Diethyl dicarbonate, 5000 ppm addition of stabilizer | | | | | | | |
|---|---|---|---|---|---|---|---|
| Temperature [° C.] | 130 | 130 | 130 | 130 | 130 | 130 | 130 |
| Diethyl dicarbonate Amount [g] | 1 | 1 | 1 | 1 | 1 | 1 | 1 |
| Addition | without | silica gel | silica gel | silica gel | silica gel | silica gel | silica gel |
| Amount [mg] | | 10 | 10 | 10 | 10 | 10 | 10 |
| Addition of stabilizer | without | without | $Al_2(SO_4)_3 \cdot 18H_2O$ | crystalline $H_3PO_4$ | 85% strength $H_3PO_4$ | sodium sulphite | Na 4-hydroxy-benzoate |
| Amount [mg] | | | 5 | 5 | 5 | 5 | 5 |
| Gas evolution [ml] | | | | | | | |
| Minute 1 | 0.5 | 2.5 | 1.7 | 1.5 | 1.8 | 3.0 | 1.0 |
| Minute 2 | 1.0 | 7.2 | 4.9 | 3.9 | 3.4 | 8.9 | 3.7 |
| Minute 5 | 1.2 | 28.9 | 13.6 | 8.6 | 7.5 | 29.5 | 19.0 |
| Minute 10 | 1.3 | 46.3 | 18.4 | 10.0 | 10.8 | 46.7 | 35.0 |
| Minute 15 | 1.3 | 50.0 | 21.2 | 12.4 | 13.0 | 50.0 | 48.5 |

TABLE 2

| Dimethyl dicarbonate, 20 000 ppm addition of stabilizer | | | | |
|---|---|---|---|---|
| Temperature [° C.] | 100 | 100 | 100 | 100 |
| Dimethyl dicarbonate Amount [g] | 1 | 1 | 1 | 1 |
| Addition | without | silica gel | silica gel | silica gel |
| Amount [mg] | | 10 | 10 | 10 |
| Addition of stabilizer | without | without | crystalline $H_3PO_4$ | 85% strength $H_3PO_4$ |
| Amount [mg] | | | 20 | 20 |
| Gas evolution [ml] | | | | |
| Minute 1 | 0.5 | 1.3 | 0.7 | 0.1 |
| Minute 2 | 1.4 | 3.9 | 1.7 | 0.3 |
| Minute 5 | 3.3 | 20.1 | 4.5 | 2.3 |
| Minute 10 | 5.7 | 49.0 | 10.8 | 9.6 |
| Minute 15 | 8.8 | 50.0 | 16.7 | 14.4 |

TABLE 3

Dimethyl dicarbonate, 1670 ppm addition of stabilizer

| Temperature [° C.] | 100 | 100 | 100 | 100 | 100 | 100 | 100 | 100 | 100 |
|---|---|---|---|---|---|---|---|---|---|
| Dimethyl dicarbonate Amount [g] | 3 | 3 | 3 | 3 | 3 | 3 | 3 | 3 | 3 |
| Addition | without | silica gel | silica gel | silica gel | silica gel | silica gel | silica gel | silica gel | silica gel |
| Amount [mg] | without | 10 | 10 | 10 | 10 | 10 | 10 | 10 | 10 |
| Addition of stabilizer | without | without | water | boric acid | $Al_2(SO_4)_3 \cdot 18H_2O$ | crystalline $H_3PO_4$ | 85% strength $H_3PO_4$ | $B_2O_3$ | phytic acid |
| Amount [mg] | | | 5 | 5 | 5 | 5 | 5 | 5 | 5 |
| Gas evolution [ml] | | | | | | | | | |
| Minute 1 | 0.1 | 1.0 | 2.4 | 0.2 | 1.5 | 0.1 | 0.1 | 0.4 | 1.7 |
| Minute 2 | 0.2 | 3.4 | 8.0 | 1.4 | 5.5 | 0.2 | 0.4 | 2.1 | 4.7 |
| Minute 5 | 0.6 | 20.3 | 26.8 | 7.8 | 31.5 | 0.9 | 0.9 | 9.8 | 11.0 |
| Minute 10 | 0.8 | 46.1 | 50.0 | 18.5 | 40.6 | 1.5 | 1.2 | 22.6 | 16.3 |
| Minute 15 | 1.3 | 50.0 | 50.0 | 34.1 | 50.0 | 2.3 | 1.6 | 32.9 | 19.9 |

| Temperature [° C.] | 100 | 100 | 100 | 100 | 100 | 100 | 100 | 100 |
|---|---|---|---|---|---|---|---|---|
| Dimethyl dicarbonate Amount [g] | 3 | 3 | 3 | 3 | 3 | 3 | 3 | 3 |
| Addition | silica gel | silica gel | silica gel | silica gel | silica gel | silica gel | silica gel | silica gel |
| Amount [mg] | 10 | 10 | 10 | 10 | 10 | 10 | 10 | 10 |
| Addition of stabilizer | phosphorus pentoxide | $NaH_2PO_4 \cdot H_2O$ | disodium hydrogen phosphate | Ca-phosphoryl-choline chloride·$4H_2O$ | 2-phosphono-butane-1,2,4-tricarboxylic acid $Na_2$ salt | 2-phosphono-butane-1,2,4-tricarboxylic acid in $H_2O$ 50% | oleyl phosphate (mono- and diester mixture) | diammonium hydrogenphosphate |
| Amount [mg] | 5 | 5 | 5 | 5 | 5 | 5 | 5 | 5 |
| Gas evolution [ml] | | | | | | | | |
| Minute 1 | 1.1 | 1.4 | 0.5 | 0.9 | 1.0 | 0.9 | 1.4 | 0.9 |
| Minute 2 | 3.1 | 4.4 | 1.9 | 3.2 | 3.5 | 3.2 | 3.7 | 3.2 |
| Minute 5 | 4.9 | 18.2 | 12.4 | 16.7 | 12.1 | 6.9 | 9.7 | 12.6 |
| Minute 10 | 5.7 | | | 30.3 | 28.8 | 7.9 | 15.0 | 26.1 |
| Minute 15 | 6.1 | | | 40.3 | 45.1 | 9.5 | 19.1 | 36.2 |

| Temperature [° C.] | 100 | 100 | 100 | 100 | 100 | 100 | 100 | 100 | 100 |
|---|---|---|---|---|---|---|---|---|---|
| Dimethyl dicarbonate Amount [g] | 3 | 3 | 3 | 3 | 3 | 3 | 3 | 3 | 3 |
| Addition | silica gel | silica gel | silica gel | silica gel | silica gel | silica gel | silica gel | silica gel | silica gel |
| Amount [mg] | 10 | 10 | 10 | 10 | 10 | 10 | 10 | 10 | 10 |
| Addition of stabilizer | Phosphorous acid + pyrophosphoric acid | dimethyl phosphate | trimethyl phosphate | pyrophosphoric acid | phosphorous acid | $H_3PO_2$ in $H_2O$ 50% | aminotris-methylene-phosphonic acid in $H_2O$ 50% | diethylenetriamine-pentamethylene-phosphonic acid in $H_2O$ 35% and HCl 15% | $PCl_3$ |
| Amount [mg] | 2.5 + 2.5 | 5 | 5 | 5 | 5 | 5 | 5 | 5 | 5 |
| Gas evolution [ml] | | | | | | | | | |
| Minute 1 | 0.2 | 0.2 | 0.3 | 0.3 | 0.3 | 0.1 | 1.2 | 0.6 | 0.9 |
| Minute 2 | 0.5 | 0.9 | 1.4 | 1.0 | 0.9 | 0.3 | 4.3 | 1.5 | 1.9 |
| Minute 5 | 1.3 | 2.4 | 8.0 | 1.6 | 2.0 | 1.2 | 10.8 | 2.6 | 2.8 |
| Minute 10 | 2.0 | | | 1.9 | 3.4 | 4.6 | 16.8 | 3.5 | 3.5 |
| Minute 15 | 3.2 | | | 2.4 | 4.9 | 26.1 | 21.4 | 4.5 | 4.3 |

TABLE 4

Dimethyl dicarbonate, 1670 ppm addition of stabilizer

| Temperature [° C.] | 100 | 100 | 100 | 100 | 100 | 100 | 100 | 100 |
|---|---|---|---|---|---|---|---|---|
| Dimethyl dicarbonate Amount [g] | 3 | 3 | 3 | 3 | 3 | 3 | 3 | 3 |
| Addition | without | manganese dioxide | manganese dioxide | manganese dioxide | manganese dioxide | manganese dioxide | manganese dioxide | manganese dioxide |
| Amount [mg] | | 10 | 10 | 10 | 10 | 10 | 10 | 10 |
| Addition of stabilizer | without | without | crystalline $H_3PO_4$ | 85% strength $H_3PO_4$ | phosphorus pentoxide | 2-phosphono-butane-1,2,4-tricarboxylic acid in $H_2O$ 50% | diethylenetriamine-pentamethylene-phosphonic acid in $H_2O$ 35% and HCl 15% | water |
| Amount [mg] | | | 5 | 5 | 5 | 5 | 5 | 5 |

TABLE 4-continued

| Dimethyl dicarbonate, 1670 ppm addition of stabilizer | | | | | | | | |
|---|---|---|---|---|---|---|---|---|
| Gas evolution [ml] | | | | | | | | |
| Minute 1 | 0.1 | 3.8 | 0.2 | 1.0 | 0.6 | 1.4 | 1.5 | 7.1 |
| Minute 2 | 0.2 | 9.3 | 0.8 | 2.1 | 1.5 | 3.9 | 3.1 | 26.4 |
| Minute 5 | 0.6 | 21.7 | 1.4 | 3.9 | 2.5 | 8.2 | 6.8 | 35.4 |
| Minute 10 | 0.8 | 31.1 | 1.8 | 5.4 | 2.9 | 11.4 | 9.7 | 46.1 |
| Minute 15 | 1.3 | 41.5 | 2.3 | 6.4 | 3.4 | 12.9 | 12.1 | 50.0 |

TABLE 5

| Dimethyl dicarbonate, 1670 ppm addition of stabilizer | | | |
|---|---|---|---|
| Temperature [° C.] | 100 | 100 | 100 |
| Dimethyl dicarbonate Amount [g] | 3 | 3 | 3 |
| Addition | without | surface of the flask highly internally scratched | surface of the flask highly internally scratched |
| Addition of stabilizer | without | without | 85% strength $H_3PO_4$ |
| Amount [mg] | | | 5 |
| Gas evolution [ml] | | | |
| Minute 1 | 0.1 | 4.0 | 1.7 |
| Minute 2 | 0.2 | 6.0 | 2.6 |
| Minute 5 | 0.6 | 7.6 | 3.4 |
| Minute 10 | 0.8 | 10.0 | 4.8 |
| Minute 15 | 1.3 | 11.0 | 5.5 |

TABLE 6

| Dimethyl dicarbonate, <1000 ppm addition of stabilizer | | | | |
|---|---|---|---|---|
| Temperature [° C.] | 100 | 100 | 100 | 100 |
| Dimethyl dicarbonate Amount [g] | 3 | 3 | 3 | 3 |
| Addition | silica gel | silica gel | silica gel | silica gel |
| Amount [mg] | 10 | 10 | 10 | 10 |
| Addition of stabilizer | 5 ppm 85% strength $H_3PO_4$ | 10 ppm 85% strength $H_3PO_4$ | 50 ppm 85% strength $H_3PO_4$ | 100 ppm 85% strength $H_3PO_4$ |
| Gas evolution [ml] | | | | |
| Minute 1 | 1.5 | 0.7 | 1.1 | 1.3 |
| Minute 2 | 4.0 | 1.9 | 2.2 | 2.6 |
| Minute 5 | 14.3 | 6.8 | 5.3 | 4.9 |
| Minute 10 | 32.2 | 25.0 | 8.2 | 6.5 |
| Minute 15 | | 39.9 | 10.9 | 7.1 |

EXAMPLE 2

Dimethyl dicarbonate was stored at room temperature. As an index of decomposition, the dimethyl carbonate content was determined by GC. Without addition of a stabilizer composition, the dimethyl carbonate content of the sample was 1090 ppm after 3 months.

The experiment was repeated, but approximately 5 ppm of phosphoric acid were added. The experimental series was carried out using 10 different samples. The dimethyl carbonate content in this case after 3 months was on average only 210 ppm.

What is claimed is:

1. A process for the purification by distillation of a diester of dicarbonic acid, comprising:

admixing the diester of dicarbonic acid having a structure conforming to the general formula (I)

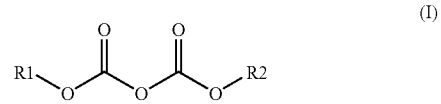

where $R^1$ and $R^2$ independently of one another are straight-chain or branched $C_1$-$C_8$-alkyl, cycloalkyl, $C_2$-$C_8$-alkenyl, $C_2$-$C_8$-alkynyl or benzyl, each of which is optionally monosubstituted to polysubstituted, identically or differently by halogen; nitro; cyano; $C_1$-$C_6$-alkoxy; or dialkylamino; and/or are phenyl which is optionally monosubstituted to polysubstituted, identically or differently by halogen; nitro; cyano; alkyl; haloalkyl; alkoxy; haloalkoxy; acyl; acyloxy; alkoxycarbonyl; or carboxyl, with 0.01 to 3000 ppm of one or more phosphorus compounds, wherein the phosphorus compounds comprise at least one phosphorus-oxygen bond, thereby forming a mixture; and subsequently distilling the mixture.

2. A process for the purification by distillation of a diester of dicarbonic acid, comprising:

admixing the diester of dicarbonic acid having a structure conforming to the general formula (I)

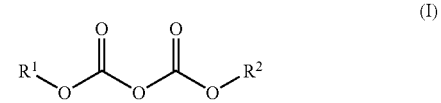

where $R^1$ and $R^2$ independently of one another are straight-chain or branched $C_1$-$C_8$-alkyl, cycloalkyl, $C_2$-$C_8$-alkenyl $C_2$-$C_8$-alkynyl or benzyl, each of which is optionally monosubstituted to polysubstituted, identically or differently by halogen; nitro; cyano; $C_1$ -$C_6$-alkoxy; or dialkylamino; and/or are phenyl which is optionally monosubstituted to polysubstituted, identically or differently by halogen; nitro; cyano; alkyl; haloalkyl; alkoxy; haloalkoxy; acyl; acyloxy; alkoxycarbonyl; or carboxyl, with 0.01 to 3000 ppm of one or more phosphorus compounds wherein the phosphorus compounds are those selected from phosphorus oxides, phosphorus-oxygen acids, and mixtures thereof, thereby forming a mixture; and subsequently distiiling the mixture.

3. A process for the purification by distillation of a diester of dicarbonic acid, comprising:

admixing the diester of dicarbonic acid having a structure conforming to the general formula (I)

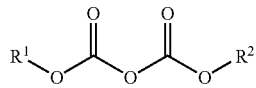

(I)

where

R¹ and R² independently of one another are strairght-chain or branched $C_1$-$C_8$-alkyl, cycloalkyl, $C_2$-$C_8$-alkenyl $C_2$-$C_8$-alkynyl or benzyl, each of which is optionally monosubstituted to polysubstituted, identically or differently by halogen; nitro; cyano; $C_1$-$C_6$-alkoxy; or dialkylamino; and/or are phenyl which is optionally monosubstituted to polysubstituted, identically or differently by halogen; nitro; cyano; alkyl; haloalkyl; alkoxy; haloalkoxy; acyl; acyloxy; alkoxycarbonyl; or carboxyl, with 0.01 to 3000 ppm of one or more phosphorus compounds, wherein said phosphorus compounds are selected from $P_2O_5$, $H_3PO_2$, $H_3PO_3$, aqueous or crystalline $H_3PO_4$, pyrophosphoric acid, metaphosphoric acid, polyphosphoric acids, dimethyl phosphate, trimethyl phosphate, sodium hydrogen phosphates, ammonium hydrogen phosphates, oleyl phosphate, phytic acid, phosphorylcholine, adenosine 3'-monophosphoric acid, 2-phosphonobutane-1,2,4-tricarboxylic acid, aminotrismethylenephosphonic acid, diethylenetriaminepentamethylenephosphonic acid, phosphorus trichloride, phosphoryl chloride, and phosphonic-acid-group-containing ion exchangers, thereby forming a mixture; and subsequently distilling the mixture.

4. The process as in any one of claims 1, 2, and 3, wherein the diester of dicarbonic acid is dimethyl dicarbonate or diethyl dicarbonate.

5. The process as in any one of claims 1, 2, and 3, wherein the phosphorus compounds are present in an amount of 0.01 to 2,000 ppm, based on diesters of dicarbonic acid.

6. The process as in any one of claims 1, 2, and 3, wherein said distilling step is performed at a pressure of 5 to 100 mbar and a temperature of between 30 and 120° C.

* * * * *